United States Patent
Zhu et al.

(10) Patent No.: US 11,614,466 B2
(45) Date of Patent: Mar. 28, 2023

(54) DETECTION CIRCUIT FOR A NERVE STIMULATOR

(71) Applicant: SCENERAY CO., LTD., Jiangsu (CN)

(72) Inventors: Weiran Zhu, Jiangsu (CN); Caijun Li, Jiangsu (CN)

(73) Assignee: SCENERAY CO., LTD, Jiangsu (CN)

( * ) Notice: Subject to any disclaimer, the term of this patent is extended or adjusted under 35 U.S.C. 154(b) by 0 days.

(21) Appl. No.: 17/633,690

(22) PCT Filed: Nov. 25, 2019

(86) PCT No.: PCT/CN2019/120463
§ 371 (c)(1),
(2) Date: Feb. 8, 2022

(87) PCT Pub. No.: WO2021/062931
PCT Pub. Date: Apr. 8, 2021

(65) Prior Publication Data
US 2022/0317204 A1 Oct. 6, 2022

(30) Foreign Application Priority Data
Sep. 30, 2019 (CN) .......................... 201921662695.4

(51) Int. Cl.
*A61N 1/36* (2006.01)
*G01R 1/30* (2006.01)
*G01R 31/54* (2020.01)

(52) U.S. Cl.
CPC ............ *G01R 1/30* (2013.01); *A61N 1/36125* (2013.01); *A61N 1/36128* (2013.01); *G01R 31/54* (2020.01)

(58) Field of Classification Search
CPC ............ A61N 1/36125; A61N 1/36128; A61N 1/36142; G01R 31/54
See application file for complete search history.

(56) References Cited

U.S. PATENT DOCUMENTS 4,088,141 A 5/1978 Niemi

FOREIGN PATENT DOCUMENTS

| CN | 203422416 U | 2/2014 |
|---|---|---|
| CN | 107802958 A | 3/2018 |

(Continued)

OTHER PUBLICATIONS

Written Opinion of the International Searching Authority dated Jun. 22, 2020, for related International Application No. PCT/CN2019/120463.

(Continued)

*Primary Examiner* — Paula J Stice
(74) *Attorney, Agent, or Firm* — Burns & Levinson, LLP; Joseph M. Maraia

(57) ABSTRACT

A detection circuit includes an open circuit detection branch and a current detection branch. The open circuit detection branch includes a comparator and a digital logic branch. A positive input terminal of the comparator is connected to one end of the sampling resistor adjacent to the stimulation source, a negative input terminal of the comparator is connected to one end of the sampling resistor facing away from the stimulation source, and an output terminal of the comparator is connected to the digital logic branch. The current detection branch includes an amplifier and a first switch. A negative input terminal of the amplifier is connected to the one end of the sampling resistor facing away from the stimulation source, an output terminal of the amplifier is connected to a control terminal of the first switch.

7 Claims, 2 Drawing Sheets

(56) References Cited

FOREIGN PATENT DOCUMENTS

| CN | 109669066 A | 4/2019 |
|---|---|---|
| CN | 110870944 A | 3/2020 |

OTHER PUBLICATIONS

International Preliminary Report on Patentability dated Apr. 5, 2022, for related International Application No. PCT/CN2019/120463.

International Search Report from related PCT Application No. PCT/CN2019/120463, dated Jun. 22, 2020 (4 pages; 2 in Chinese and 2 in English).

DETECTION CIRCUIT FOR A NERVE STIMULATOR

CROSS-REFERENCE TO RELATED APPLICATIONS

This is a national stage application filed under 37 U.S.C. 371 based on International Patent Application No. PCT/CN2019/120463, filed Nov. 25, 2019, which claims priority to Chinese Patent Application No. 201921662695.4 filed Sep. 30, 2019, the disclosures of which are incorporated herein by reference in their entireties.

TECHNICAL FIELD

The present disclosure relates to the technical field of medical equipment and, in particular, to a detection circuit for a nerve stimulator.

BACKGROUND

In implantable medical devices, a nerve stimulator can effectively control the symptoms of functional neurological diseases and psychosis by performing chronic electrical stimulation on a target nerve. The nerve stimulator is in contact with the human body through electrodes and has multiple stimulation branches that share a main constant current source, and the main constant current source is a stimulation source. Therefore, under a normal operation condition, each stimulation branch is constant with a current kept at a set value. If one or more of the multiple stimulation branches are disconnected, the currents of the other branches that are not disconnected are greater than the set value, which may likely cause damage to human tissues.

Therefore, it is necessary to design a detection circuit to detect the connection and current distribution of each stimulation branch.

SUMMARY

To solve one of the preceding problems, the present disclosure provides a detection circuit for a nerve stimulator. The nerve stimulator includes a stimulation source and a stimulation branch communicated with the stimulation source. A sampling resistor is disposed in the stimulation branch. The detection circuit includes an open circuit detection branch and a current detection branch. The open circuit detection branch includes a comparator and a digital logic branch. A positive input terminal of the comparator is connected to one end of the sampling resistor adjacent to the stimulation source, a negative input terminal of the comparator is connected to one end of the sampling resistor facing away from the stimulation source, and an output terminal of the comparator is connected to the digital logic branch. When the stimulation branch is an open circuit, the comparator is configured to output a low level, and when the stimulation branch is a closed circuit, the comparator is configured to output a high level. The current detection branch includes an amplifier and a first switch. A negative input terminal of the amplifier is connected to the one end of the sampling resistor facing away from the stimulation source, an output terminal of the amplifier is connected to a control terminal of the first switch, two connection terminals of the first switch are connected to a first resistor and a second resistor, respectively, another end of the first resistor is connected to the stimulation source, another end of the second resistor is grounded, and a positive input terminal of the amplifier is connected to one end of the first resistor adjacent to the first switch. When the first switch is turned on, an output voltage between two ends of the second resistor is proportional to a current on the sampling resistor.

Further, the detection circuit includes a first operational amplifier, when the first operational amplifier is used as the comparator, the first operational amplifier has a comparison state; and when the first operational amplifier is used as the amplifier, the first operational amplifier has a following state.

Further, the detection circuit further includes a second switch and a third switch, where the second switch and the third switch each are a single pole, double throw switch; a fixed end of the second switch is connected to a positive input terminal of the first operational amplifier, and two moving ends of the second switch are connected to the sampling resistor and the first resistor, respectively, to switch between the open circuit detection branch and the current detection branch; a fixed end of the third switch is connected to an output terminal of the first operational amplifier, and two moving ends of the third switch are connected to the digital logic branch and the control terminal of the first switch, respectively, to switch between the open circuit detection branch and the current detection branch.

Further, a first operational amplifier circuit is disposed in the first operational amplifier and includes an offset voltage calibration circuit, the offset voltage calibration circuit includes a first MOS tube branch connected in parallel with a positive input terminal of the first operational amplifier and a second MOS tube branch connected in parallel with a negative input terminal of the first operational amplifier, the first MOS tube branch includes a first MOS tube and the second MOS tube branch includes a second MOS tube, a gate of the second MOS tube is connected to an output terminal of the first operational amplifier circuit, and a gate of the first MOS tube is connected to a reference voltage; the offset voltage calibration circuit further includes a first capacitor, and two ends of the first capacitor are connected between the gate of the second MOS tube and a ground, respectively.

Further, the first operational amplifier further includes a voltage divider circuit, the voltage divider circuit includes a third resistor and a fourth resistor connected in series with the third resistor, another end of the third resistor is connected to the stimulation source, and another end of the fourth resistor is grounded; the gate of the first MOS tube is connected between the third resistor and the fourth resistor, and the reference voltage is a voltage of the fourth resistor; the offset voltage calibration circuit further includes a second capacitor, and two ends of the second capacitor are connected between the gate of the first MOS tube and the ground, respectively.

Further, the offset voltage calibration circuit further includes a fourth switch and a fifth switch, the fourth switch is connected between an output terminal of the first operational amplifier and the first capacitor, and the fifth switch is connected between the reference voltage and a second capacitor.

Further, a first operational amplifier circuit is disposed in the first operational amplifier and further includes a built-in gain circuit, the built-in gain circuit includes a fifth resistor, a sixth resistor and a sixth switch, the fifth resistor and the sixth resistor are connected to the stimulation source, the sixth switch is a single pole, double throw switch; and a moving end of the sixth switch is separately connected to another end of the fifth resistor and another end of the sixth resistor, and a fixed end of the sixth switch is connected to an output terminal of the first operational amplifier.

Further, a resistance of the sixth resistor is greater than a resistance of the fifth resistor; when the moving end of the sixth switch is connected to the fifth resistor, the open circuit detection branch is a closed circuit and the current detection branch is an open circuit; and when the moving end of the sixth switch is connected to the sixth resistor, the open circuit detection branch is an open circuit and the current detection branch is a closed circuit.

Further, the detection circuit further includes a second operational amplifier, where a positive input terminal of the second operational amplifier is connected to one end of the second resistor facing away from a ground, and a negative input terminal of the second operational amplifier is connected to an output terminal of the second operational amplifier.

Compared with the existing art, the open circuit detection branch and the current detection branch in the detection circuit can separately detect the stimulation branch to determine whether multiple stimulation branches are disconnected or current values are abnormal, which is convenient for a user to make adjustments to prevent excessive current from causing damage to human tissues.

DETAILED DESCRIPTION

For a better understanding of solutions in the present disclosure by those skilled in the art, the technical solutions in embodiments of the present disclosure will be described clearly and completely in conjunction with the drawings in the embodiments of the present disclosure. Apparently, the embodiments described below are part, not all, of embodiments. Based on the embodiments described herein, all other embodiments obtained by those of ordinary skill in the art on the premise that no creative work is done are within the scope of the present disclosure.

The present disclosure provides a detection circuit for a nerve stimulator. The nerve stimulator is an implantable medical device and can effectively control the symptoms of functional neurological diseases and psychosis by performing chronic electrical stimulation on a target nerve. Moreover, the nerve stimulator generally has multiple stimulation branches that share one stimulation source VDDH, each stimulation branch is provided with a sampling resistor Rs, and multiple detection circuits are also provided and connected to multiple stimulation branches, respectively. In this embodiment, as shown in FIG. 1, for ease of display, only one detection circuit is shown in the figure.

Figure 1:
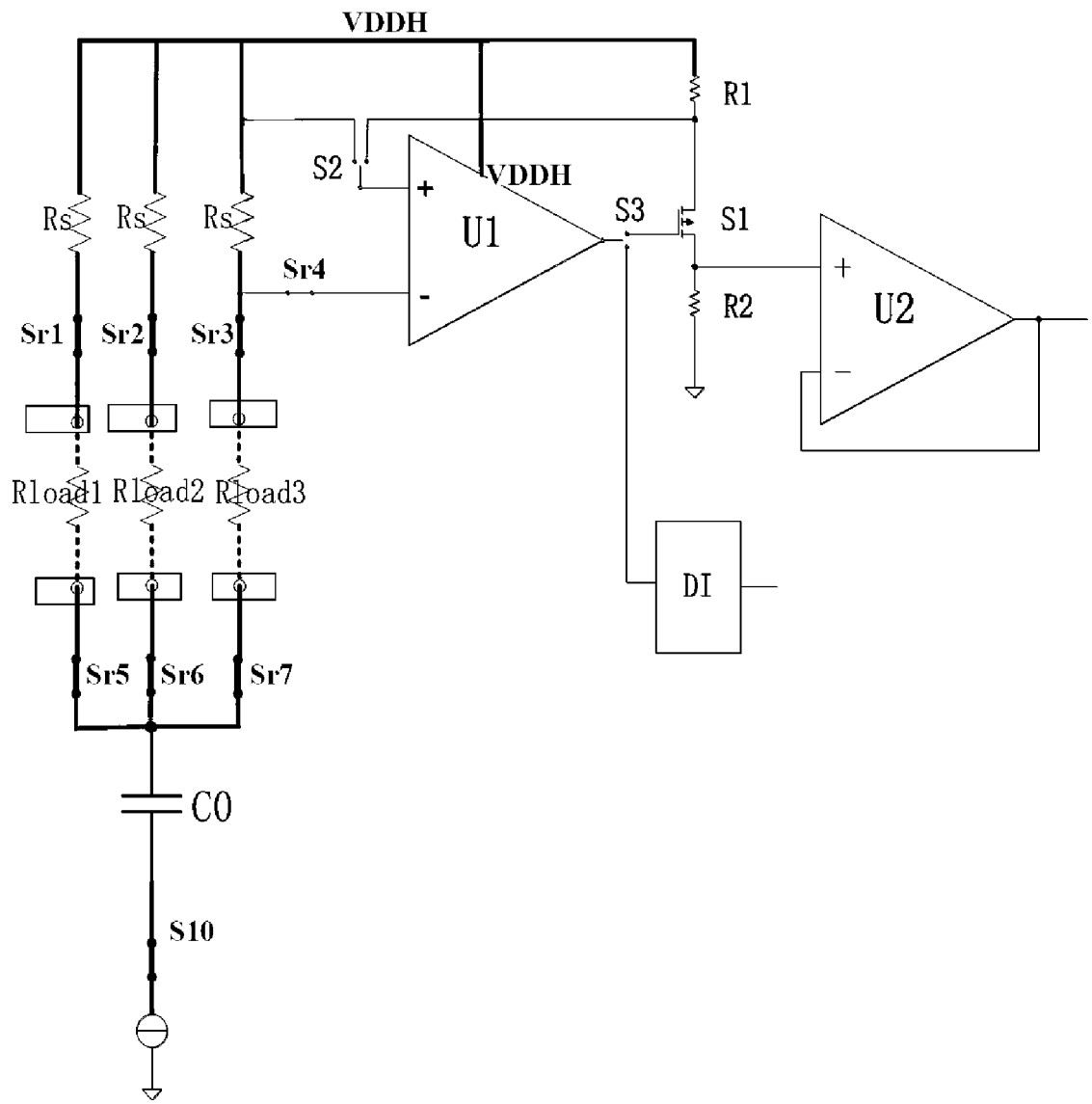
FIG. 1 is a circuit diagram of a detection circuit for a nerve stimulator according to the present disclosure.
Figure 2:
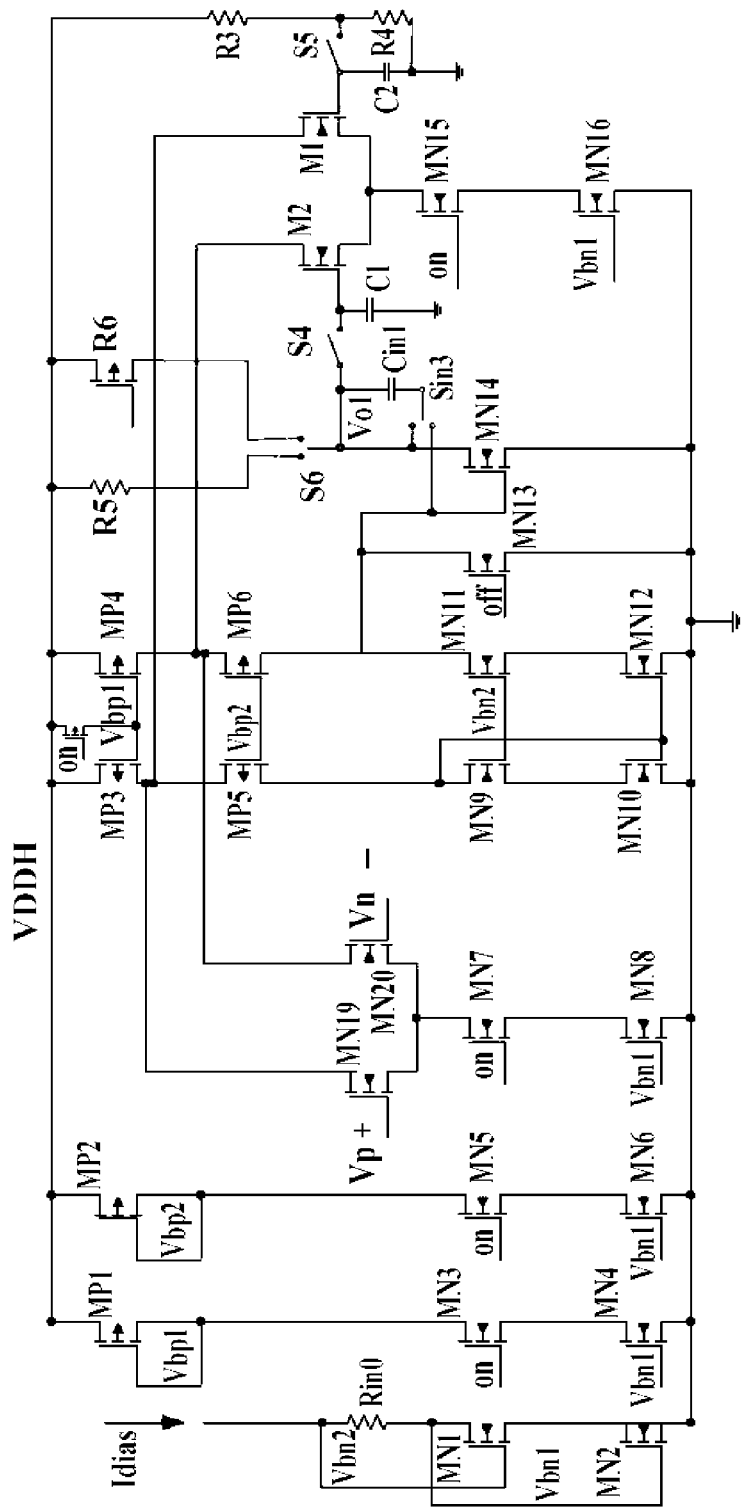
FIG. 2 is a circuit diagram of a first operational amplifier according to the present disclosure.

As shown in FIGS. 1 to 2, the detection circuit includes an open circuit detection branch and a current detection branch.

The open circuit detection branch includes a comparator U1 and a digital logic branch DI. A positive input terminal of the comparator U1 is connected to one end of the sampling resistor Rs adjacent to the stimulation source VDDH, a negative input terminal of the comparator U1 is connected to one end of the sampling resistor Rs facing away from the stimulation source VDDH, and an output terminal of the comparator U1 is connected to the digital logic branch DI. In the case where the stimulation branch is an open circuit, the comparator U1 outputs a low level, and in the case where the stimulation branch is a closed circuit, the comparator U1 outputs a high level.

The current detection branch includes an amplifier U1 and a first switch S1. A negative input terminal of the amplifier U1 is connected to the one end of the sampling resistor Rs facing away from the stimulation source VDDH, and an output terminal of the amplifier U1 is connected to a control terminal of the first switch S1. Two connection terminals of the first switch S1 are connected to a first resistor R1 and a second resistor R2, respectively, the other end of the first resistor R1 is connected to the stimulation source VDDH, and the other end of the second resistor R2 is grounded. A positive input terminal of the amplifier U1 is connected to one end of the first resistor R1 adjacent to the first switch S1. In the case where the first switch S1 is turned on, an output voltage between two ends of the second resistor R2 is proportional to a current on the sampling resistor Rs.

Therefore, the open circuit detection branch and the current detection branch are integrated in the preceding detection circuit so that an on-off condition of the stimulation branch and a magnitude of the current on the stimulation branch can both be detected. The following is described in details.

The comparator U1 is used in the open circuit detection branch. When a voltage at the positive input terminal of the comparator U1 is greater than a voltage at the negative input terminal of the comparator U1, the output terminal of the comparator U1 outputs a high level. When the voltage at the positive input terminal of the comparator U1 is less than the voltage at the negative input terminal of the comparator U1, the output terminal of the comparator U1 outputs a low level. In this embodiment, the positive input terminal and the negative input terminal of the comparator U1 are connected in parallel with two ends of the sampling resistor Rs, respectively. When the stimulation branch where the sampling resistor Rs is located is an open circuit, no current flows through the stimulation branch and thus the output terminal of the comparator U1 outputs a low level. When the stimulation branch where the sampling resistor Rs is located is a closed circuit, a current flows through the stimulation branch, a voltage at the one end of the sampling resistor Rs adjacent to the stimulation source VDDH is greater than a voltage at the one end of the sampling resistor Rs facing away from the stimulation source VDDH, and thus the output terminal of the comparator U1 outputs a high level. The open circuit detection branch further includes the digital logic branch DI. After the output terminal of the comparator U1 outputs a high level or a low level, the high level or the low level signal is converted into a digital logic signal through the open circuit detection branch. The high level corresponds to "1", and the low level corresponds to "0", which allows the user to easily determine whether the stimulation branch is a short circuit or an open circuit.

The amplifier U1 is used in the current detection branch. In this embodiment, on the one hand, an output voltage of the amplifier U1 is high enough to control the two connection terminals of the first switch S1 to communicate with each other. On the other hand, a voltage at the positive input terminal of the amplifier U1 is equal to a voltage at the negative input terminal of the amplifier U1. Therefore, a voltage between two ends of the sampling resistor Rs is equal to a voltage between two ends of the first resistor R1. A current passing through the sampling resistor Rs is denoted by Is, and then a voltage Us between two ends of the sampling resistor Rs is described by the following formula.

$$U_s = I_s \times R_s$$

Moreover, since the voltage at the positive input terminal of the amplifier U1 is equal to the voltage at the negative input terminal of the amplifier U1, a current $I_1$ passing through the first resistor R1 and the second resistor R2 is described by the following formula.

$$\frac{I_s \times R_s}{R1}$$

Then, a voltage $U_2$ at the second resistor R2 is described by the following formula.

$$\frac{I_s \times R_s \times R2}{R1}$$

Therefore, it can be seen from the preceding formulas that the voltage at the second resistor R2 is proportional to the current on the sampling resistor Rs so that the magnitude of the current on the sampling resistor Rs can be determined.

Moreover, in this embodiment, to make the output more stable, the detection circuit further includes a second operational amplifier U2. A positive input terminal of the second operational amplifier U2 is connected to one end of the second resistor R2 facing away from the ground, and a negative input terminal of the second operational amplifier U2 is connected to an output terminal of the second operational amplifier U2. In this embodiment, the second operational amplifier U2 is also used as a follower so that an output terminal voltage of the second operational amplifier U2 is consistent with the voltage $U_2$ of the second resistor R2. Therefore, the output terminal voltage of the second operational amplifier U2 is also proportional to the current Is on the sampling resistor Rs so that the current Is on the sampling resistor Rs can be measured, and thus whether the current Is on the sampling resistor Rs is within a specified range can be determined.

As shown in FIG. 1, the detection circuit includes a first operational amplifier U1. When the first operational amplifier U1 is used as the comparator UI, the first operational amplifier U1 has a comparison state; when the first operational amplifier U1 is used as the amplifier U1, the first operational amplifier U1 has a following state. Therefore, the first operational amplifier U1 is used as both the comparator U1 and the amplifier U1. In the present disclosure, functions of the comparator U1 and the amplifier U1 can be achieved by switching the first operational amplifier U1 between different states so that only one first operational amplifier U1 can achieve both open circuit detection and current detection, thereby enhancing the integration of the circuit. Of course, if two operational amplifiers are used as a comparator and an amplifier, respectively, the object of the present disclosure can also be achieved.

Since the open circuit detection branch and the current detection branch share one first operational amplifier U1, other branches connected to the first operational amplifier U1 are also slightly changed. In this embodiment, at least two switches are used to achieve the implementation.

The detection circuit further includes a second switch S2 and a third switch S3, where each the second switch S2 and the third switch S3 are a single pole, double throw switch. The single pole, double throw switch has a moving end and a fixed end, and the moving end can move between two connection terminals for connection to different circuits. A fixed end of the second switch S2 is connected to a positive input terminal of the first operational amplifier U1, and two moving ends of the second switch S2 are connected to the sampling resistor Rs and the first resistor R1, respectively, to switch between the open circuit detection branch and the current detection branch. A fixed end of the third switch S3 is connected to an output terminal of the first operational amplifier U1, and two moving ends of the third switch S3 are connected to the digital logic branch DI and a control terminal of the first resistor R1, respectively, to switch between the open circuit detection branch and the current detection branch. Therefore, the further cooperation with the second switch S2 and the third switch S3 makes it easier to switch between the open circuit detection branch and the current detection branch. Moreover, it is to be noted that in this embodiment, two single pole, double throw switches are used. If four single pole, single throw switches are used for connection to different branches, the object of the present disclosure can also be achieved.

A first operational amplifier circuit is disposed in the first operational amplifier U1. The first operational amplifier U1 generally has an offset voltage. However, in the open circuit detection and current detection, the offset voltage outputted through the first operational amplifier U1 has a relatively great impact on a detection result. Therefore, the offset voltage of the first operational amplifier U1 needs to be calibrated.

It is known that the offset voltage is caused by the asymmetry of a circuit structure in the operational amplifier. Therefore, when the positive input terminal and the negative input terminal of the operational amplifier are short-circuited or connected to the same level, the output terminal of the operational amplifier still has a certain voltage output.

As shown in FIG. 2, the first operational amplifier circuit includes an offset voltage calibration circuit. The offset voltage calibration circuit includes a first MOS tube branch connected in parallel with a positive input terminal Vp+ of the first operational amplifier U1 and a second MOS tube branch connected in parallel with a negative input terminal Vn− of the first operational amplifier U1. The first MOS tube branch includes a first MOS tube M1 and the second MOS tube branch includes a second MOS tube M2. A gate of the second MOS tube M2 is connected to an output terminal of the first operational amplifier circuit, and a gate of the first MOS tube M1 is connected to a reference voltage. The offset voltage calibration circuit further includes a first capacitor C1, where two ends of the first capacitor C1 are connected to the gate of the second MOS tube M2 and the ground, respectively.

In this embodiment, the first MOS tube M1 and the second MOS tube M2 are designed symmetrically so that when the positive input terminal and the negative input terminal of the first operational amplifier U1 are short-circuited or connected to the same level, a voltage value Vo at the output terminal of the first operational amplifier U1 is similar to a value of the reference voltage; but due to the existence of the offset voltage, a difference exists between the voltage value Vo at the output terminal and the value of the reference voltage. Then, due to the existence of the first capacitor C1, the voltage value Vo at the output terminal of the first operational amplifier U1 is stored in the first capacitor C1. The first MOS tube M1 is connected in parallel with the positive input terminal Vp+, and the second MOS tube M2 is connected in parallel with the negative input terminal Vn− so that when the positive input terminal Vp+ and the negative input terminal Vn− have inputs, the reference voltage and the voltage stored in the first capacitor C1 can pre-adjust voltages at the positive input terminal Vp+ and the negative input terminal Vn− and remove the offset voltage in advance.

In this embodiment, the reference voltage is obtained through voltage division. The first operational amplifier circuit further includes a voltage divider circuit, and the voltage divider circuit includes a third resistor R3 and a fourth resistor R4 connected in series with the third resistor R3. The other end of the third resistor R3 is connected to the stimulation source VDDH, and the other end of the fourth resistor R4 is grounded. The gate of the first MOS tube M1 is connected between the third resistor R3 and the fourth resistor R4, and the reference voltage is the voltage of the fourth resistor R4. Moreover, a voltage value of the stimulation source VDDH may fluctuate, which causes the value of the reference voltage to fluctuate. If the value of the reference voltage fluctuates, the voltage value Vo at the output terminal of the first operational amplifier U1 and the magnitude of the offset voltage are affected. Therefore, the offset voltage calibration circuit further includes a second capacitor C2, where two ends of the second capacitor C2 are connected to the gate of the first MOS tube M1 and the ground, respectively. Therefore, when the positive input terminal and the negative input terminal of the first operational amplifier U1 are short-circuited, the preceding reference voltage is stored in the second capacitor C2 and remains constant without changing.

Of course, to ensure that the voltage at the output terminal of the first operational amplifier U1 and the reference voltage can be better stored in the first capacitor C1 and the second capacitor C2 and do not affect other circuit branches, the offset voltage calibration circuit further includes a fourth switch S4 and a fifth switch S5. The fourth switch S4 is connected between the output terminal of the first operational amplifier U1 and the first capacitor C1, and the fifth switch S5 is connected between the reference voltage and the second capacitor C2.

Therefore, before both the open circuit detection and the current detection, the offset voltage of the first operational amplifier U1 needs to be calibrated. The fourth switch S4 and the fifth switch S5 are firstly turned on so that the voltage at the output terminal of the first operational amplifier U1 and the reference voltage can be stored in the first capacitor C1 and the second capacitor C2, respectively. Then, the fourth switch S4 and the fifth switch S5 are turned off so that voltage values of the first capacitor C1 and the second capacitor C2 can act on the negative input terminal and the positive input terminal of the first operational amplifier U1 through the second MOS tube M2 and the first MOS tube M1, thereby no longer affecting the output terminal of the first operational amplifier U1 and not being affected by the fluctuation of the stimulation source VDDH.

In addition, the first operational amplifier U1 has a very large operational gain. However, if the operational gain is relatively large during the open circuit detection, the voltage at the output terminal of the first operational amplifier U1 is easily affected, resulting in errors with respect to determination of the high level or the low level. Therefore, the first operational amplifier circuit further includes a built-in gain circuit. The built-in gain circuit includes a fifth resistor R5, a sixth resistor R6 and a sixth switch S6, and the fifth resistor R5 and the sixth resistor R6 are connected to the stimulation source VDDH. The sixth switch S6 is a single pole, double throw switch. A moving end of the sixth switch S6 is separately connected to the other end of the fifth resistor R5 and the other end of the sixth resistor R6, and a fixed end of the sixth switch S6 is connected to the output terminal of the first operational amplifier U1.

Of course, the resistance of the sixth resistor R6 is greater than the resistance of the fifth resistor R5. In the case where the moving end of the sixth switch S6 is connected to the fifth resistor R5, the open circuit detection branch is a closed circuit and the current detection branch is an open circuit. In the case where the moving end of the sixth switch S6 is connected to the sixth resistor R6, the open circuit detection branch is an open circuit and the current detection branch is a closed circuit. Therefore, during the open circuit detection, the open circuit detection branch is a closed circuit, and the output terminal of the first operational amplifier U1 is connected to the fifth resistor R5 with a relatively small resistance so that the operational gain is reduced and errors during the open circuit detection can be prevented. Moreover, in this embodiment, the sixth resistor R6 is connected to the circuit in a form of an MOS tube.

Therefore, to sum up, through the preceding configuration, the open circuit detection branch and the current detection branch in the detection circuit can separately detect the stimulation branch to determine whether multiple stimulation branches are disconnected or current values are abnormal, which is convenient for a user to make adjustments to prevent excessive current from causing damage to human tissues. On the other hand, the open circuit detection branch and the current detection branch are differently connected to the first operational amplifier U1 so that the comparator U1 and the amplifier U1 are formed. With the cooperation of the second switch S2 and the third switch S3, the integration of the whole detection circuit can be further improved. Finally, the offset voltage is calibrated before the formal detection so that the impact of the offset voltage on the detection result is reduced and thus the detection result is more accurate.

Moreover, it is to be understood that although this specification is described in terms of the embodiments, not every embodiment includes only one independent technical solution. Such description mode of the specification is merely for the sake of clarity, and those skilled in the art should regard the specification as a whole. The technical solutions in the embodiments may also be appropriately combined to form other embodiments which are understood by those skilled in the art.

The series of detailed descriptions listed above are merely specific descriptions of feasible embodiments of the present disclosure and are not intended to limit the protection scope of the present disclosure. Any equivalent embodiments or variations made without departing from the technical spirit of the present disclosure should be included within the protection scope of the present disclosure.

What is claimed is:

1. A detection circuit for a nerve stimulator, wherein the nerve stimulator comprises a stimulation source and a stimulation branch communicated with the stimulation source, a sampling resistor is disposed in the stimulation branch; and the detection circuit comprises:
   an open circuit detection branch comprising a comparator and a digital logic branch, wherein a positive input terminal of the comparator is connected to one end of the sampling resistor adjacent to the stimulation source, a negative input terminal of the comparator is connected to one end of the sampling resistor facing away from the stimulation source, and an output terminal of the comparator is connected to the digital logic branch; when the stimulation branch is an open circuit, the comparator is configured to output a low level, and when the stimulation branch is a closed circuit, the comparator is configured to output a high level; and a current detection branch comprising an amplifier and a first switch, wherein a negative input terminal of the amplifier is connected to the one end of the sampling resistor facing away from the stimulation source, an output terminal of the amplifier is connected to a control terminal of the first switch, two connection terminals of the first switch are connected to a first resistor and a second resistor, respectively, another end of the first resistor is connected to the stimulation source, another end of the second resistor is grounded, and a positive input terminal of the amplifier is connected to one end of the first resistor adjacent to the first switch; when the first switch is turned on, an output voltage between two ends of the second resistor is proportional to a current on the sampling resistor;

wherein the detection circuit further comprises a first operational amplifier, wherein when the first operational amplifier is used as the comparator, the first operational amplifier has a comparison state; and when the first operational amplifier is used as the amplifier, the first operational amplifier has a following state;

wherein a first operational amplifier circuit is disposed in the first operational amplifier and comprises a built-in gain circuit, the built-in gain circuit comprises a fifth resistor, a sixth resistor and a sixth switch, the fifth resistor and the sixth resistor are connected to the stimulation source, the sixth switch is a single pole, double throw switch; and a moving end of the sixth switch is separately connected to another end of the fifth resistor and another end of the sixth resistor, and a fixed end of the sixth switch is connected to an output terminal of the first operational amplifier.

2. The detection circuit of claim 1, further comprising a second switch and a third switch, wherein the second switch and the third switch each are a single pole, double throw switch; a fixed end of the second switch is connected to a positive input terminal of the first operational amplifier, and two moving ends of the second switch are connected to the sampling resistor and the first resistor, respectively, to switch between the open circuit detection branch and the current detection branch; a fixed end of the third switch is connected to an output terminal of the first operational amplifier, and two moving ends of the third switch are connected to the digital logic branch and the control terminal of the first switch, respectively, to switch between the open circuit detection branch and the current detection branch.

3. The detection circuit of claim 1, wherein the first operational amplifier circuit further comprises an offset voltage calibration circuit, the offset voltage calibration circuit comprises a first MOS tube branch connected in parallel with a positive input terminal of the first operational amplifier and a second MOS tube branch connected in parallel with a negative input terminal of the first operational amplifier, the first MOS tube branch comprises a first MOS tube and the second MOS tube branch comprises a second MOS tube, a gate of the second MOS tube is connected to an output terminal of the first operational amplifier circuit, and a gate of the first MOS tube is connected to a reference voltage; the offset voltage calibration circuit further comprises a first capacitor, and two ends of the first capacitor are connected between the gate of the second MOS tube and a ground, respectively.

4. The detection circuit of claim 3, wherein the first operational amplifier further comprises a voltage divider circuit, the voltage divider circuit comprises a third resistor and a fourth resistor connected in series with the third resistor, another end of the third resistor is connected to the stimulation source, and another end of the fourth resistor is grounded; the gate of the first MOS tube is connected between the third resistor and the fourth resistor, and the reference voltage is a voltage of the fourth resistor; the offset voltage calibration circuit further comprises a second capacitor, and two ends of the second capacitor are connected between the gate of the first MOS tube and the ground, respectively.

5. The detection circuit of claim 3, wherein the offset voltage calibration circuit further comprises a fourth switch and a fifth switch, the fourth switch is connected between an output terminal of the first operational amplifier and the first capacitor, and the fifth switch is connected between the reference voltage and a second capacitor.

6. The detection circuit of claim 1, wherein a resistance of the sixth resistor is greater than a resistance of the fifth resistor; when the moving end of the sixth switch is connected to the fifth resistor, the open circuit detection branch is a closed circuit and the current detection branch is an open circuit; and when the moving end of the sixth switch is connected to the sixth resistor, the open circuit detection branch is an open circuit and the current detection branch is a closed circuit.

7. The detection circuit of claim 1, further comprising a second operational amplifier, wherein a positive input terminal of the second operational amplifier is connected to one end of the second resistor facing away from a ground, and a negative input terminal of the second operational amplifier is connected to an output terminal of the second operational amplifier.

* * * * *